United States Patent [19]

Drabek et al.

[11] 4,250,190
[45] Feb. 10, 1981

[54] (O-(N-METHYLCARBAMOYL)-OXIME)-(N,N,N-TRIALKYLUREA)-N,N-SULFIDE DERIVATIVES, PROCESSES FOR PRODUCING THEM, COMPOSITIONS CONTAINING THESE DERIVATIVES AS ACTIVE INGREDIENTS, AND THE USE THEREOF FOR CONTROLLING INSECT PESTS

[75] Inventors: Jozef Drabek, Oberwil, Switzerland; Manfred Böger, Weil am Rhine, Fed. Rep. of Germany

[73] Assignee: Ciba-Geigy Corporation, Ardsley, N.Y.

[21] Appl. No.: 68,300

[22] Filed: Aug. 30, 1979

[30] Foreign Application Priority Data

Aug. 31, 1978 [CH] Switzerland .................. 9198/78
Mar. 13, 1979 [CH] Switzerland .................. 2377/79
Jun. 11, 1979 [CH] Switzerland .................. 5433/79

[51] Int. Cl.³ .................... A01N 37/18; C07C 69/708
[52] U.S. Cl. ............................ 424/298; 260/453 RW
[58] Field of Search ................ 260/453 RW; 424/298

[56] References Cited

U.S. PATENT DOCUMENTS 3,825,579   7/1974   Fujimoto ............... 260/453 RW

Primary Examiner—Henry R. Jiles
Assistant Examiner—Robert C. Whittenbaugh
Attorney, Agent, or Firm—Frederick H. Rabin

[57] ABSTRACT

Compounds of the formula I

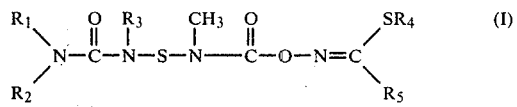

wherein $R_1$ and $R_2$ are each $C_1$–$C_4$-alkyl or $C_3$–$C_6$-cycloalkyl, $R_3$ is $C_1$–$C_8$-alkyl or $C_3$–$C_6$-cycloalkyl, $R_4$ is $C_1$–$C_3$-alkyl or allyl and $R_5$ is methyl or —CO—NR$_6$(R$_7$) wherein $R_6$ and $R_7$ are each hydrogen or methyl, possess valuable pesticidal in particular insecticidal properties.

9 Claims, No Drawings

(O-(N-METHYLCARBAMOYL)-OXIME)-(N,N,N-TRIALKYLUREA)-N,N-SULFIDE DERIVATIVES, PROCESSES FOR PRODUCING THEM, COMPOSITIONS CONTAINING THESE DERIVATIVES AS ACTIVE INGREDIENTS, AND THE USE THEREOF FOR CONTROLLING INSECT PESTS

The present invention relates to novel (O-(N-methyl-carbamoyl)-oxime)-(N',N'',N''-trialkylurea)-N,N'-sulfide derivatives which have an action against insect pests, to processes for producing these derivatives, to insecticidal compositions containing them as active ingredients, and to processes for the control of insect pests by application of the novel compounds.

From the Belgian Patent Specification No. 855,928 are already known, inter alia, compounds of the formula $$\text{alkyl}\,O-\overset{\overset{O}{\|}}{C}-\overset{\overset{\text{alkyl}}{|}}{N}-S-\overset{\overset{CH_3}{|}}{N}-\overset{\overset{O}{\|}}{C}-O-N=C\overset{S\text{alkyl}}{\underset{CH_3}{}}$$

as insecticides.

According to the present invention, there are provided novel compounds of this type which likewise have an action against pests, particularly against insect pests, and which, by virtue of their advantageous biological properties, are especially suitable for practical application.

The novel (O-(N-methyl-carbamoyl)-oxime)-(N',N'',N''-trialkylurea)-N,N'-sulfide derivatives according to the invention correspond to the formula I $$\overset{R_1}{\underset{R_2}{}}N-\overset{\overset{O}{\|}}{C}-\overset{\overset{R_3}{|}}{N}-S-\overset{\overset{CH_3}{|}}{N}-\overset{\overset{O}{\|}}{C}-O-N=C\overset{SR_4}{\underset{R_5}{}} \quad (I)$$

wherein
- $R_1$ and $R_2$ are each a $C_1$–$C_4$-alkyl group or $C_3$–$C_6$-cycloalkyl group,
- $R_3$ is a $C_1$–$C_8$-alkyl group or $C_3$–$C_6$-cycloalkyl group,
- $R_4$ is a $C_1$–$C_3$-alkyl group or allyl group, and
- $R_5$ is a methyl group, or a group of the formula $$\overset{R_6}{\underset{R_7}{}}N-CO-$$

wherein $R_6$ and $R_7$ are each hydrogen or methyl.

Alkyl groups as $R_1$ and $R_2$, which are identical or different, and also as $R_3$ and $R_4$ can be branched-chain or straight-chain. Substituents of this type are for example: the methyl, ethyl, n- and i-propyl group, and the n-, i-, s- and t-butyl group, and also the n-pentyl, n-hexyl and n-octyl group, and isomers thereof.

Preferred types of substituents and combinations of these among each other in the compounds of the formula I are as follows:
(1) for $R_1$ and $R_2$: $C_1$–$C_4$-alkyl, particularly methyl and ethyl, and especially methyl;
(2) for $R_3$: $C_1$–$C_8$-alkyl or cyclopropyl, in particular $C_1$–$C_4$-alkyl or cyclopropyl;
(3) for $R_4$: methyl and ethyl, and
(4) for $R_5$: methyl.

In accordance with the present invention it has now surprisingly been found that the said compounds of the formula I have an excellent insecticidal action with a broad spectrum. They can for example be used for controlling insects of the orders Lepidoptera, Colleoptera, Heteroptera, Diptera, Orthoptera and Homoptera.

It is to be emphasised in this connection that the compounds of the formula I are characterised by a particularly strongly marked activity against insects of the orders Lepidoptera and Homoptera, and especially against insects of the families Noctuidae and Aphididae. It has in this respect been found for example that the compounds according to the invention have both a contact and a systemic action against a considerable number of representatives of the families mentioned (for example *Spodoptera littoralis, Heliothis virescens, Aphis fabae, Aphis craccivora* and *Myzus persicae*), which can be controlled only with great difficulty using other agents.

By virtue of these properties, the compounds of the formula I are particularly suitable for controlling insects, especially insects which damage plants, in crops of useful plants and ornamental plants, principally in the field of vegetable and fruit cultivation, including citrus fruits.

Furthermore, the compounds of the formula I have a valuable action against acarids which damage plants (mites, for example of the family Tetranychidae) and also against phytoparasitic nematodes.

It has also be verified according to the invention that the pesticidal properties described in the foregoing are coupled with a toxicity to warm-blooded animals which is advantageously low for practical application in the field of plant protection.

The compounds of the formula I are produced by processes analogous to known processes, for example by reacting (a) a compound of the formula II $$\overset{R_1}{\underset{R_2}{}}N-\overset{\overset{O}{\|}}{C}-\overset{\overset{R_3}{|}}{N}-S-\overset{\overset{CH_3}{|}}{N}-COX' \quad (II),$$

in the presence of a base, with a compound of the formula III $$HO-N=C\overset{SR_4}{\underset{R_5}{}} \quad (III);$$

or (b) a compound of the formula IV $$\overset{R_1}{\underset{R_2}{}}N-\overset{\overset{O}{\|}}{C}-\overset{\overset{R_3}{|}}{N}-SX'' \quad (IV),$$

in the presence of a base, with a compound of the formula V, $$\begin{array}{c} CH_3 \\ \diagdown \\ H \end{array} N-\overset{O}{\underset{\|}{C}}-O-N=C \begin{array}{c} \diagup SR_4 \\ \diagdown R_5 \end{array} \quad (V),$$

the symbols $R_1$ to $R_5$ in the formulae II, III, IV and V having the meanings already given for formula I, X' being a halogen atom, particularly a fluorine atom, and X" being a halogen atom, especially a chlorine atom.

The processes (a) and (b) are performed at a reaction temperature of between $-50°$ and $+130°$ C., preferably between $-10°$ and $+100°$ C., under normal or slightly elevated pressure, and in the presence of a solvent or diluent which is inert to the reactants.

Bases suitable for these processes are in particular: tertiary amines, such as trialkylamines, pyridines and dialkylanilines, also hydroxides, oxides, carbonates and bicarbonates of alkali metals and alkaline-earth metals, as well as alkali metal alcoholates, for example potassium tert-butylate and sodium methylate.

Suitable solvents or diluents are for example: ethers and ethereal compounds, such as diethyl ether, di-isopropyl ether, dioxane and tetrahydrofuran; aliphatic and aromatic hydrocarbons, especially benzene, toluene and xylenes; and ketones, such as acetone, methyl ethyl ketone and cyclohexanone.

The starting materials of the formulae III, IV and V used in the processes described in the foregoing are known, and they can be produced by methods analogous to known methods (see for example G.B. Patent Specification No. 1,138,347; U.S. Pat. Nos. 3,474,171 and 3,111,539 and German Offenlegungsschrift No. 1,910,588).

The starting materials of the formula II are however novel and likewise form part of the subject matter of the invention. They are obtained from known precursors, for example according to the following reaction pattern:

$$\left[ \begin{array}{c} R_1 \diagdown \quad \diagup R_3 \\ N-CO-N \\ R_2 \diagup \quad + \quad \diagdown SCl \\ CH_3NH-COX' \end{array} \right] \xrightarrow[-50° \text{ C. to room temperature}]{\substack{\text{base (e.g. triethylamine)} \\ \text{solvent (e.g. toluene)}}} (II)$$

The compounds of the formula I are used according to the invention on their own, or they form a constituent of compositions which also contain suitable carriers or additives or mixtures of such substances. Suitable carriers and additives can be solid or liquid and they correspond to the substances common in formulation practice, such as natural or regenerated substances, solvents dispersing agents, wetting agents, adhesives, thickeners, binders and/or fertilisers.

The insecticidal action of the compositions according to the invention can be substantially broadened by the addition of other acaricides and/or insecticides. Suitable additives are for example: organic phosphorus compounds; nitrophenols and derivatives thereof; formamidines; ureas; pyrethrin-like compounds; carbamates and chlorinated hydrocarbons.

The compositions according to the invention can be in the form of dusts, granulates, dispersions, solutions and suspensions, as well as in the form of water-dispersible wettable powders, pastes, emulsions and emulsion concentrates, and can be applied in these forms.

The content of active substance (compound of the formula I) in the compositions described above is between 0.1 and 95%; it is to be mentioned in this connection that with application from an aeroplane, or by means of other suitable application devices, also higher concentrations can be used.

The compounds of the formula I can be formulated for example as follows:

Emulsion Concentrate I 20 parts by weight of the active substance are dissolved in 70 parts by weight of xylene, and to the solution are added 10 parts by weight of an emulsifying agent consisting of a mixture of an arylphenylpolyglycol ether and the calcium salt of dodecylbenzenesulfonic acid.

Water can be added in any proportion to the emulsion concentrate to form a milky emulsion.

Emulsion Concentrate II 5 to a maximum of 30 parts by weight of active substance are dissolved at room temperature, with stirring, in
30 parts by weight of dibutylphthalate,
10 parts by weight of Solvent 200 (low-viscous, highly aromatic petroleum distillate),
15 to 35 parts by weight of Dutrex 238 FC (viscous highly aromatic petroleum distillate), and to the solution are added
10 parts by weight of an emulsifier mixture consisting of castor-oil polyglycol ether and the calcium salt of dodecylbenzenesulfonic acid.

The emulsion concentrate thus obtained produces milky emulsions when water is added.

Wettable Powder 5 to 30 parts by weight of the active substance are thoroughly mixed, in a mixing apparatus, with
5 parts by weight of an absorbing carrier material (Kieselsäaure K 320 [silicic acid] or Wessalon S) and
55 to 80 parts by weight of a carrier material (bolus alba or Kaolin B 24) and a dispersing agent mixture consisting of
5 parts by weight of a sodium lauryl sulfonate and
5 parts by weight of an alkyl-aryl-polyglycol ether.

This mixture is ground to 5–15 μm in a dowelled disc mill or air jet mill. A good suspension is obtained by adding water to the wettable powder thus produced.

Dust 5 parts by weight of finely ground active substance are thoroughly mixed with
2 parts by weight of a precipitated silicic acid and
93 parts by weight of talc.

Pour-on Solution

| | |
|---|---|
| active substance | 30.0 g |
| sodium dioctylsulfosuccinate | 3.0 g |
| benzyl alcohol | 48.0 g |
| peanut oil | 19.8 g |
| | 100.8 g = 100 ml |

The active substance is dissolved in the benzyl alcohol with stirring and if necessary with slight heating. The sodium dioctylsulfosuccinate and peanut oil are added to the solution, and are dissolved with heating and thorough stirring.

The Examples which follow serve to further illustrate the invention.

EXAMPLE 1

(a) Production of (N-methylcarbamoylfluoride)-(N',N'',N'''-trimethylurea)-N,N'-sulfide (starting material)

14.85 ml of methylisocyanate was added at a temperature of −50° C., with stirring, to a solution of 5 g of anhydrous hydrofluoric acid in 5 ml of toluene, and the reaction mixture was subsequently stirred for 2 hours. To the solution obtained in this manner was added 42.1 g of N,N,N'-trimethylurea sulfonyl chloride, and at a temperature of −50° to −20° C. there was added dropwise, with stirring, 34.55 ml of triethylamine. The reaction mixture was afterwards stirred for 2 hours at −20° C. and then for 10 hours at room temperature. After filtration under suction, the filtrate was concentrated in a rotary evaporator. The crude product was distilled off under high vacuum to obtain (N-methylcarbamoylfluoride)-(N',N'',N'''-trimethylurea)-N,N'-sulfide of the formula

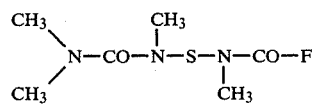

as an orange-coloured liquid having a b.p. of 78°–83° C. at 0.04 mb.

The following compounds of the formula IIa

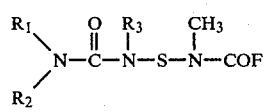

are obtainable in an analogous manner.

| $R_1$ | $R_2$ | $R_3$ | Physical data |
|---|---|---|---|
| $C_2H_5$ | $C_2H_5$ | $CH_3$ | b.p. : 97–99° C./0,11 mb |
| n-$C_4H_9$ | n-$C_4H_9$ | $CH_3$ | b.p. : 119–124° C./0,08 mb |
| $CH_3$ | $CH_3$ | n-$C_4H_9$ | b.p. :105–110° C./0,08 mb |

| $R_1$ | $R_2$ | $R_3$ | Physical data |
|---|---|---|---|
| $CH_3$ | $CH_3$ | n-$C_6H_{13}$ | b.p. : 125–127° C./0,09 mb |
| $CH_3$ | $CH_3$ | n-$C_8H_{17}$ | b.p. : 140–145° C./0,13 mb |
| $CH_3$ | $CH_3$ | ▷— | b.p. : 100–150° C./0,09 mb |
| n-$C_4H_9$ | n-$C_4H_9$ | n-$C_4H_9$ | b.p. : 135–136° C./0,07 mb |
| $C_2H_5$ | $C_2H_5$ | n-$C_4H_9$ | b.p. : 120–121° C./0,08 mb |
| n-$C_3H_7$ | n-$C_3H_7$ | $CH_3$ | b.p. : 109–111° C./0,07 mb |
| i-$C_3H_7$ | i-$C_3H_7$ | $CH_3$ | b.p. : 96–103° C./0,11–0,2 mb |
| n-$C_4H_9$ | $CH_3$ | n-$C_4H_9$ | b.p. : 125–128° C./0,07 mb |

(b) Production of (O-(N-methylcarbamoyl)-methylthioacetaldoxime)-(N',N'',N'''-trimethylurea)-N,N'-sulfide (final product)

To a solution of 5.6 g of 1-methylthioacetaldoxime in 100 ml of benzene and 20 ml of chloroform was added, with stirring, 7.5 ml of triethylamine, and subsequently there was added dropwise, at a maximum temperature of 30° C., 11.15 g of (N-methylcarbamoylfluoride)-(N',N'',N'''-trimethylurea)-N,N'-sulfide. The reaction mixture was subsequently stirred for 16 hours at room temperature and for 2 hours at 45° C.; it was then filtered under suction, and the filtrate was washed with water. The organic phase was concentrated by evaporation, and to the residue was added an ether/hexane mixture. The crystals which had precipitated were filtered off under suction, washed with ether and hexane and dried. There was obtained in this manner (O-(N-methylcarbamoyl)-1-methylthioacetaldoxime)-(N',N'',N'''-trimethylurea)-N,N'-sulfide of the formula (Compound No. 1)

in the form of colourless crystals having a m.p. of 112°–115° C. of 112°–115° C.

The following compounds of the formula I can be produced by a process analogous to the production processes described in the foregoing:

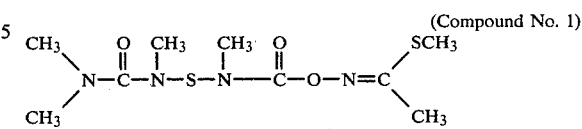

| Comp. No. | $R_1$ | $R_2$ | $R_3$ | $R_4$ | $R_5$ | Physical data |
|---|---|---|---|---|---|---|
| 2 | $CH_3$ | $CH_3$ | $CH_3$ | $C_2H_5$ | $CH_3$ | $n_D^{45}$ : 1,5243 |
| 3 | $CH_3$ | $CH_3$ | $CH_3$ | i-$C_3H_7$ | $CH_3$ | $n_D^{45}$ : 1,5203 |
| 4 | $CH_3$ | $CH_3$ | $CH_3$ | $CH_2$=CH—$CH_2$— | $CH_3$ | $n_D^{45}$ : 1,5390 |
| 5 | $C_2H_5$ | $C_2H_5$ | $CH_3$ | $CH_3$ | $CH_3$ | $n_D^{40}$ : 1,5238 |
| 6 | n-$C_4H_9$ | n-$C_4H_9$ | n-$C_4H_9$ | $CH_3$ | $CH_3$ | $n_D^{20}$ : 1,4937 |
| 7 | n-$C_4H_9$ | n-$C_4H_9$ | $CH_3$ | $CH_3$ | $CH_3$ | $n_D^{20}$ : 1,5143 |
| 8 | $CH_3$ | $CH_3$ | n-$C_4H_9$ | $CH_3$ | $CH_3$ | m.p. : 75–78° C. |
| 9 | $CH_3$ | $CH_3$ | n-$C_4H_9$ | $C_2H_5$ | $CH_3$ | $n_D^{20}$ : 1,5118 |
| 10 | $CH_3$ | $CH_3$ | n-$C_4H_9$ | $CH_2$=CH—$CH_2$— | $CH_3$ | $n_D^{40}$ : 1,5169 |
| 11 | $CH_3$ | $CH_3$ | n-$C_6H_{13}$ | $CH_3$ | $CH_3$ | $n_D^{20}$ : 1,5108 |
| 12 | $CH_3$ | $CH_3$ | n-$C_6H_{13}$ | $C_2H_5$ | $CH_3$ | $n_D^{20}$ : 1,5076 |
| 13 | $CH_3$ | $CH_3$ | n-$C_6H_{13}$ | i-$C_3H_7$ | $CH_3$ | $n_D^{20}$ : 1,5070 |
| 14 | $CH_3$ | $CH_3$ | n-$C_8H_{17}$ | $CH_3$ | $CH_3$ | $n_D^{30}$ : 1,5032 |
| 15 | $CH_3$ | $CH_3$ | n-$C_8H_{17}$ | $C_2H_5$ | $CH_3$ | $n_D^{30}$ : 1,4997 |
| 16 | $CH_3$ | $CH_3$ | n-$C_8H_{17}$ | i-$C_3H_7$ | $CH_3$ | $n_D^{30}$ : 1,4988 |

-continued

| Comp. No. | R₁ | R₂ | R₃ | R₄ | R₅ | Physical data |
|---|---|---|---|---|---|---|
| 17 | CH₃ | CH₃ | cyclopropyl | CH₃ | CH₃ | $n_D^{45}$: 1,5339 |
| 18 | CH₃ | CH₃ | cyclopropyl | CH₂=CH—CH₂— | CH₃ | $n_D^{40}$: 1,5381 |
| 19 | CH₃ | CH₃ | cyclopropyl | C₂H₅ | CH₃ | $n_D^{40}$: 1,5279 |
| 20 | i-C₃H₇ | i-C₃H₇ | CH₃ | CH₃ | CH₃ | $n_D^{30}$: 1,5178 |
| 21 | i-C₃H₇ | i-C₃H₇ | CH₃ | C₂H₅ | CH₃ | $n_D^{30}$: 1,5124 |
| 22 | CH₃ | CH₃ | CH₃ | CH₃ | —CONH₂ | m.p. 141–145° C. |
| 23 | CH₃ | CH₃ | n-C₄H₉ | CH₃ | —CONH₂ | solid |
| 24 | n-C₃H₇ | n-C₃H₇ | CH₃ | CH₃ | CH₃ | $n_D^{20}$: 1,5219 |
| 25 | n-C₃H₇ | n-C₃H₇ | CH₃ | C₂H₅ | CH₃ | $n_D^{20}$: 1,5170 |
| 26 | CH₃ | CH₃ | cyclopropyl | CH₃ | —CONH₂ | m.p. 165–171° C. |
| 27 | n-C₄H₉ | n-C₄H₉ | CH₃ | C₂H₅ | CH₃ | $n_D^{20}$: 1,5119 |
| 28 | C₂H₅ | C₂H₅ | n-C₄H₉ | C₂H₅ | CH₃ | $n_D^{20}$: 1,5055 |
| 29 | CH₃ | CH₃ | CH₃ | CH₃ | —CON(CH₃)₂ | m.p. 116–119° C. |
| 30 | CH₃ | CH₃ | n-C₄H₉ | CH₃ | —CON(CH₃)₂ | $n_D^{40}$: 1,5210 |
| 31 | CH₃ | CH₃ | n-C₆H₁₃ | CH₃ | —CON(CH₃)₂ | $n_D^{40}$: 1,5122 |
| 32 | CH₃ | CH₃ | n-C₈H₁₇ | CH₃ | —CON(CH₃)₂ | $n_D^{40}$: 1,5069 |
| 33 | CH₃ | CH₃ | cyclopropyl | CH₃ | —CON(CH₃)₂ | $n_D^{40}$: 1,5323 |
| 34 | n-C₄H₉ | CH₃ | n-C₄H₉ | CH₃ | CH₃ | $n_D^{20}$: 1,5026 |
| 35 | n-C₄H₉ | CH₃ | n-C₄H₉ | C₂H₅ | CH₃ | $n_D^{20}$: 1,5002 |
| 36 | n-C₄H₉ | CH₃ | n-C₄H₉ | i-C₃H₇ | CH₃ | $n_D^{20}$: 1,4982 |
| 37 | n-C₄H₉ | n-C₄H₉ | n-C₄H₉ | C₂H₅ | CH₃ | $n_D^{20}$: 1,4954 |
| 38 | n-C₄H₉ | n-C₄H₉ | n-C₄H₉ | CH₃ | —CONH₂ | $n_D^{40}$: 1,5070 |
| 39 | C₂H₅ | C₂H₅ | n-C₄H₉ | CH₃ | CH₃ | $n_D^{40}$: 1,5087 |

EXAMPLE 2

Insecticidal stomach poison action: *Spodoptera littoralis, Dysdercus fasciatus* and *Heliothis virescens*

Cotton plants were sprayed with an aqueous emulsion containing 0.05% of the compound to be tested (obtained from a 10% emulsifiable concentrate). After drying of the coating, larvae of the species *Spodoptera littoralis* (L3 stage), *Dysdercus fasciatus* (L4) and *Heliothis virescens* (L3), respectively, were settled on the plants. Two plants were used for each test compound and for each test species, and an assessment of the destruction of larvae was made 2, 4, 24 and 48 hours after commencement of the test. The tests were carried out at 24° C. with 60% relative humidity.

Compounds of the formula I according to Example 1 exhibited in the above test a good action against larvae of the species *Spodoptera littoralis, Dysdercus fasciatus* and *Heliothis virescens.*

EXAMPLE 3

Insecticidal stomach poison action: *Leptinotarsa decemlineata*

The test described in Example 2 was repeated using larvae of the species *Leptinotarsa decemlineata* (L3) and using potato plants in place of cotton plants, the procedure otherwise remaining the same.

Compounds of the formula I exhibited in this test a good action against larvae of the species *Leptinotarsa decemlineata.*

EXAMPLE 4

Insecticidal contact action: *Myzus persicae*

Plants (*Vicia fabae*) grown in water were each infested, before the commencement of the test, with about 200 individuals of the species *Myzus persicae.* Three days later, the plants treated in this manner were sprayed from a distance of 30 cm until dripping wet with a solution containing 10 and 1 ppm, respectively, of the compound to be tested. Two plants were used for each test compound and for each concentration, and an evaluation of the attained degree of destruction of the insects was made after a further 24 hours.

Compounds of the formula I according to Example 1 exhibited in the above test a good action against insects of the species *Myzus persicae*.

EXAMPLE 5

Insecticidal systemic action: *Aphis craccivora*

Rooted bean plants were transplanted into pots containing 600 ccm of soil, and subsequently 50 ml of a solution of the compound to be tested (obtained from a 25% wettable powder) at a concentration of 25 ppm, 5 ppm and 1 ppm, respectively, was poured directly onto the soil. After 24 hours, lice of the species *Aphis craccivora* were settled onto the parts of the plants above the soil, and a plastics cylinder was placed over each plant in order to protect the lice from a possible contact or gas effect of the test substance. The evaluation of the achieved destruction of lice was made after 24 and 48 hours, respectively, after commencement of the test. Two plants, each in a separate pot, were used for each concentration dose of test substance. The test was carried out at 25° C. with 70% relative humidity.

The compounds according to Example 1 exhibited in the above test a good systemic action against insects of the species *Aphis craccivora*.

What is claimed is:

1. A compound of the formula I

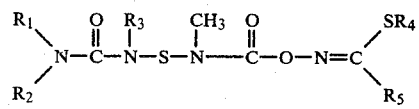

wherein $R_1$ and $R_2$ each independently of the other is $C_1$-$C_4$-alkyl or $C_3$-$C_6$-cycloalkyl, $R_3$ is $C_1$-$C_8$-alkyl or $C_3$-$C_6$-cycloalkyl, $R_4$ is $C_1$-$C_3$-alkyl or allyl and $R_5$ is methyl or a group of the formula

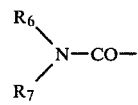

wherein $R_6$ and $R_7$ each independently of the other is hydrogen or methyl.

2. A compound as claimed in claim 1, wherein $R_5$ is methyl, aminocarbonyl or dimethylaminocarbonyl.

3. A compound as claimed in claim 2, wherein $R_1$ and $R_2$ each independently of the other is $C_1$-$C_4$-alkyl and $R_3$ is $C_1$-$C_8$-alkyl or cyclopropyl.

4. A compound as claimed in claim 3, wherein $R_1$ and $R_2$ each independently of the other is methyl or ethyl, $R_3$ is $C_1$-$C_4$-alkyl or cyclopropyl and $R_5$ is methyl.

5. A compound as claimed in claim 4 of the formula

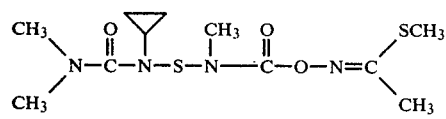

6. A compound as claimed in claim 4 of the formula

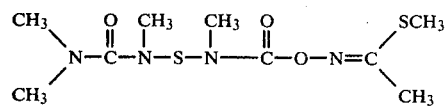

7. A compound as claimed in claim 4 of the formula

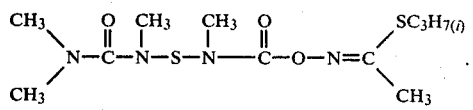

8. An insecticidal composition comprising an insecticidally effective amount of a compound as claimed in claim 1 together with an inert, solid or liquid diluent or carrier therefor.

9. A method of controlling insect pests at a locus, which method comprises applying to said locus an insecticidally effective amount of a compound as claimed in claim 1.

* * * * *